United States Patent
Trkovnik et al.

[11] Patent Number: 5,908,933
[45] Date of Patent: Jun. 1, 1999

[54] CERTAIN 4H-[1]BENZOPYRANO[3,4-B] PYRIDINE DERIVATIVES AND THEIR CORRESPONDING [6,7-B] AND [7,8-B] RING ISOMERS

[75] Inventors: Mladen Trkovnik; Zrinka Ivezić; Željko Kelnerić; Ljerka Polak, all of Zagreb, Croatia

[73] Assignee: PLIVA, farmaceutska, kemijska, prehrambena i kozmeticka industrija, dionicko drustvo, Zagreb, Croatia

[21] Appl. No.: 08/897,057

[22] Filed: Jul. 18, 1997

[30] Foreign Application Priority Data

Jul. 26, 1996 [HR] Croatia ................. P960352A

[51] Int. Cl.⁶ ............ A61K 31/44; C07D 471/04; C07D 471/02
[52] U.S. Cl. .................. 546/89; 546/64; 514/291
[58] Field of Search .................................. 546/89

[56] References Cited

U.S. PATENT DOCUMENTS 5,576,325  11/1996  Williams .................. 514/291
5,696,130  12/1997  Jones et al. .............. 514/291

Primary Examiner—Alan L. Rotman
Attorney, Agent, or Firm—Pollock, Vande Sande & Amernick

[57] ABSTRACT

The present invention relates to novel coumarin quinolone carboxylic acids wherein the pyridone system is fused in 3,4-, 6,7- and 7,8-positions of the coumarin system, of the general formula I

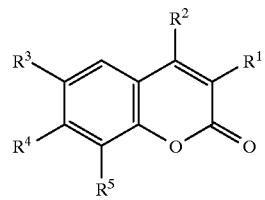

wherein
$R^1R^2$=—NHCH=C($CO_2R^6$)CO, $R^3$=$NO_2$ or $NH_2$, $R^4$=$R^5$=H, $R^6$=H or $C_2H_5$;
$R^1R^2$=—NHCH=C($CO_2R^6$)CO, $R^3$=$R^4$=H, $R^5$=F, $R^6$=H or $C_2H_5$;
$R^1R^2$=—CO($CO_2R^6$)C=CHNH, $R^3$=$R^4$=$R^5$=H, $R^6$=H or $C_2H_5$;
$R^1R^2$=$R^3R^4$=—NHCH=C($CO_2R^6$)CO, $R^5$=H, $R^6$=H or $C_2H_5$;
$R^1$=H or OH, $R^2$=$R^5$=H, $R^3R^4$=—NHCH ($CO_2R^6$)CO, $R^6$=H or $C_2H_5$;
$R^1$=OH, $R^2$=$R^3$=H, $R^4R^5$=—CO($CO_2R^6$) C=CHNH, $R^6$=H or $C_2H_5$;
$R^1$=$R^5$=H, $R^2$=$CH_3$ or $CF_3$, $R^3R^4$=—CO($CO_2R^6$)C=CHNH, $R^6$=H or $C_2H_5$,
as well as pharmaceutically acceptable salts thereof.

The object of the invention are also processes for the preparation of novel coumarin quinolone carboxylic acids and the biological action thereof.

20 Claims, No Drawings

CERTAIN 4H-[1]BENZOPYRANO[3,4-B] PYRIDINE DERIVATIVES AND THEIR CORRESPONDING [6,7-B] AND [7,8-B] RING ISOMERS

TECHNICAL FIELD

IPC: C07D 491/02

C07D 491/12

The present invention relates to novel coumarin quinolone carboxylic acids, wherein the pyridone system is fused in 3,4-, 6,7- and 7,8-positions of the coumarin system, of the general formula I

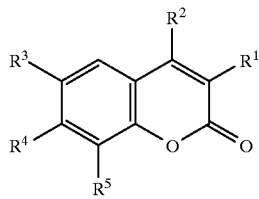

wherein $R^1R^2$=—NHCH=C(CO$_2$R$^6$)CO—R$^3$=NO$_2$ or NH$_2$, R$^4$=R$^5$=H, R$^6$=H or C$_2$H$_5$;

$R^1R^2$=—NHCH=C(CO$_2$R$^6$)CO—R$^3$=R$^4$=H, R$^5$=F, R$^6$=H or C$_2$H$_5$;

$R^1R^2$=—CO(CO$_2$R$^6$)CHNH—=R$^3$=R$^4$=R$^5$=H, R$^6$=H or C$_2$H$_5$;

$R^1R^2$=R$^3$R$^4$=NHCH=C(CO$_2$R$^6$) CO—R$^5$=H, R$^6$=H or C$_2$H$_5$;

$R^1$=H or OH, R$^2$=R$^5$=H, R$^3$R$^4$=—NHCH =C(CO$_2$R$^6$)CO—R$^6$=H or C$_2$H$_5$;

$R^1$=OH, R$^2$=R$^3$=H, R$^4$R$^5$=—CO(CO$_2$R$^6$) C=CHNH, R$^6$=H or C$_2$H$_5$;

$R^1$=R$^5$=H, R2=CH$_3$ or CF$_3$, R$^3$R$^4$=—CO(CO$_2$R$^6$)C=CHNH, R$^6$=H or C$_2$H$_5$, as well as pharmaceutically acceptable salts thereof.

The object of the invention are also processes for the preparation of the novel coumarin quinolone carboxylic acids as well as the biological action thereof.

According to the present invention novel coumarin quinolone carboxylic acids of the general formula I are prepared starting from coumarin malonate esters of the formula II disclosed in Croatian patent application P-960308A (European patent application No. . . . ) of Jul. 2, 1996

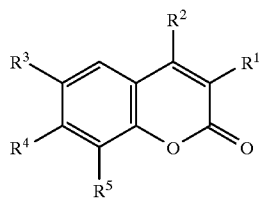

wherein $R^1$=—NHCH=C(CO$_2$C$_2$H$_5$)$_2$, R$^2$=R$^4$=H, R$^3$=H or NO$_2$, R$^5$=H or F;

$R^1$=R$^3$=—NHCH=C(CO$_2$C$_2$H$_5$)$_2$, R$^2$=R$^4$=R$^5$=H;

$R^1$=H or OH, R$^3$=—NHCH=C(CO$_2$C$_2$H$_5$)$_2$, R$^2$=R$^4$=R$^5$=H;

$R^1$=OH, R$^2$=R$^3$=R$^4$=H, R$^5$=—NHCH=C(CO$_2$C$_2$H$_5$)$_2$;

$R^1$=R$^3$=R$^5$=H, R$^2$=CH$_3$ or CF$_3$, R$^4$=—NHCH=C(CO$_2$C$_2$H$_5$)$_2$, which are heated in Dowtherm A at 250–260° C. for 10 minutes to 13 hours to obtain cyclized esters of the general formula III

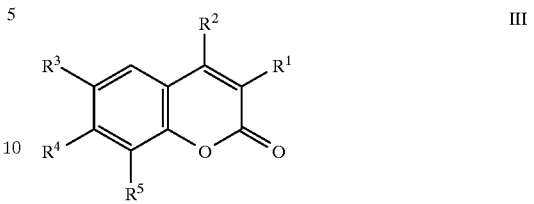

wherein $R^1R^2$=—NHCH=C(CO$_2$C$_2$H$_5$) CO, R$^3$=R$^4$=H, R$^5$=F;

$R^1R^2$=—NHCH=C(CO$_2$C$_2$H$_5$)CO, R$^3$=NO$_2$, R$^4$=R$^5$=H;

$R^1R^2$=—CO(CO$_2$C$_2$H$_5$)C=CHNH, R$^3$=R$^4$=H, R$^5$=H or F;

$R^1R^2$=R$^3$R$^4$=—NHCH=C (CO$_2$C$_2$H$_5$)CO, R$^5$=H;

$R^1$=H or OH, R$^2$=R$^5$=H, R$^3$R$^4$=—NHCH =C(CO$_2$C$_2$H$_5$)CO;

$R^1$=OH, R$^2$=R$^3$=H, R$^4$R$^5$=—CO((CO$_2$C$_2$H$_5$)C=CHNH;

$R^1$=R$^5$=H, R$^2$=CH$_3$ or CF$_3$, R$^3$R$^4$=—CO((CO$_2$C$_2$H$_5$)C=CHNH.

For the compound of the formula III wherein $R^1R^2$=—CO((CO$_2$C$_2$H$_5$)C=CHNH, R$^3$=R$^4$=H, R$^5$=H, it is expressly stated in D. T. Connor, P. A. Young, M. von Strandtman, J. *Heterocyclic Chiem.* 18 (1981) 697–702 that an attempt to cyclize the corresponding coumarin malonate ester to an ester of the formula III having the above mentioned substituents was unsuccessful and thus no corresponding acid was obtained either, said acid being, beside the ester of the formula III, also an object of the present invention and having the general formula I with the meanings $R^1R^2$=—CO(CO$_2$H)C=CHNH, R$^3$=R$^4$=H, R$^5$=H.

The compound of the formula III wherein $R^1R^2$=—NHCH=C(CO$_2$C$_2$H$_5$)CO, R$^3$=R$^4$=H, R$^5$=H (disclosed earlier in U.S. Pat. No. 4,210,758 to D. T. Connor (Warner-Lambert Company)) is at first nitrated, then reduced and finally fused with diethyl-ethoxymethylene malonate to obtain a compound of the formula IV

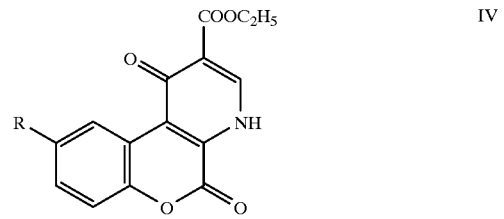

wherein R=NO$_2$ or NH$_2$.

For obtaining the compounds of the general formula I wherein $R^1R^2$=—NHCH=C (CO$_2$C$_2$H$_5$)CO, R$^3$=NH$_2$, R$^4$=R$^5$=H, the compounds of the general formula III wherein $R^1R^2$=—NHCH=C(CO$_2$C$_2$H$_5$)CO, R$^3$=NO$_2$, R$^4$=R$^5$=H are reduced in glacial acetic acid under the catalyst palladium on active carbon and in a nitrogen stream of 3 bar for a time period of 6 hours. By the hydrolysis of the compounds of the formula III, coumarin quinolone carboxylic acids of the formula I are obtained, wherein R$^1$, R$^2$, R$^3$, R$^4$ and R$^5$ have the earlier disclosed meanings and R$^6$=H.

Coumarin quinolone carboxylic acids, which are the object of the present invention, as well as pharmaceutically acceptable salts thereof are inhibitors of bacteria strains tested. In these tests a microdilution test for investigation of bacterial susceptibility according to the method NCCLS (M7-A2, Vol.10, No. 8, 1990; M100-S4, Vol. 12, No. 20, 1992) was used. Control test microorganisms employed in these experiments were S. aureus ATCC 29213, E. faecalis ATCC 29212 and P. aenrgiizosa ATCC 29213 with norfloxacin and enorfloxacin as working standards of antibiotics for comparison. The following strains were tested: Staphiloc. aureus ATCC 6538P, Bacillus subtilis NCTC 8236, Micrococcus flavus ATCC 10240, Pseudomonias aerug. NCTC 10490, Salmoizela Panama 6117, E. coli Lac+6131, E. coli Lac−6130, b-Haemol. streptococc. —B J-22, b-Haemol. streptococc. —A J-21, Streptococcus pyogenes 20F, Streptococcus faecalis ATCC 8043, E. coli ATCC 10536, Stapliyloc. epidermis ATCC 12228, B. cereus AYCC 11778, B. pumilus ATCC 8241 and B. subtilis ATCC 6633.

4,5-dihydro-4,5-dioxo- 1H-[1]benzopyrano[4,3-b]pyridine-3-carboxylic acid inhibited E. coli Lac+6131 and b-Haemol. streptococc. —A J-21.

1,5-dihydro-1,5-dioxo-7-fluoro-4H-[1]benzopyrano[3,4-b]pyridine-3-carboxylic acid inhibited the strains tested.

4,7-dihydro-4,7-dioxo-1H-[1]benzopyrano[6,7-b]pyridine-3-carboxylic acid inhibited Bacillus subtilis NCTC 8236, Streptococcus pyogeizes 20F and Streptococcus faecalis ATCC 8043.

Coumarin quinolone acids according to the present invention and pharmaceutically acceptable salts thereof were also investigated for an iil vitro antitumour action. The antitumour action was tested on the growth of cell lines of mammary cancer (MCF7), cancer of cervix uteri (HeLa), pancreas cancer (MiaPaCa2), larinx cancer (Hep2) and on normal human fibroblasts (Hef522).

1,7-dihydro-1,7-dioxo-9-(trifluoromethyl)-4H-[1]benzopyrano [6,7-b]pyridine-3-carboxylic acid inhibited the growth of the cells of mammary cancer (MCF7), pancreas cancer (MiaPaCa2) and larinx cancer (Hep2) and slightly stimulated the growth of cells of cancer of cervix uteri (HeLa) in higher concentrations. It had no significant action on the growth of fibroblasts (Hef522).

The MCF7 growth was inhibited depending on the concentration and the best inhibition was achieved at $10^{-5}$ and $10^{-8}$ M.

It had no effect on the growth of HeLa cells in the concentration range from $10^{-8}$ to $10^{-6}$ M, whereas at higher concentrations ($10^{-5}$ and $10^{-4}$ M) it stimulated their growth.

The growth of MiaPaCa2 cells was inhibited depending on the concentration. At the concentration of $10^{-4}$ M the attained inhibition was 35%.

The tested substance inhibited the growth of Hep2 cells, with increased concentration the inhibitory action was decreased and the best results were achieved in the concentration ranges of $10^{-7}$ and $10^{-5}$ M.

The tested substance exhibited no effect on the growth of normal fibroblasts (Hef522).

The invention is illustrated by the following Examples, which in no way should be construed as limitative.

EXAMPLE 1

Ethyl-1,5-dihydro- 1,5-dioxo-7-fluoro-4H-[1]benzopyrano[3,4-b]pyridine-2carboxylate

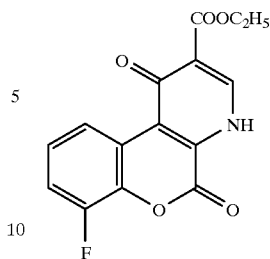

A solution of diethyl-{[(8-fluoro-2-oxo-2H-[1]-benzopyrano-3-yl) amino]-methylene} malonate (2.40 g; 0.871 mmole) in Dowtherm A (55 ml) was heated for 40 minutes at the boiling temperature. Into the cooled solution a petroleum ether having a low boiling point was added to assist with a complete precipitation of the obtained ester. The obtained precipitate of ethyl-1,5-dihydro-1,5-dioxo-7-fluoro-4H-[1]-benzopyrano[3,4-b]pyridine-2-carboxylate of a gray brown colour was washed first with petroleum ether and then with diethyl ether (1.85 g; 89%). M.p.: 288–290° C.

Analysis: calculated for $C_{15}H_{10}FNO_5$: C 59.41H 3.32N 4.62. found C 59.74H 2.97N 4.72.

$^1$H-NMR (DMSO-d$_6$)δ/ppm: 1.3 (t, CH$_3$); 4.3 (q, CH$_2$); 6.8–7.6 (m, Ar H); 8.3 (s, Py H); 9.3 (d, NH).

EXAMPLE 2

Ethyl-4,5-dihydro-4,5-dioxo-1H-[1]-benzopyrano[3,4-b]pyridine-3-carboxylate

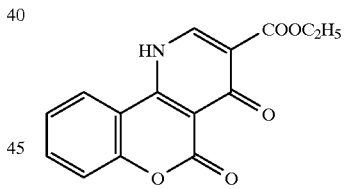

It was prepared according to the method disclosed in Example 1 starting from diethyl-{[(2-oxo-4H-[1]-benzopyrano-3-yl)amino]methylene} malonate (3.96 g; 0.012 mole). Duration of the reaction: 13 hours. Ethyl-4,5-dihydro-4,5-dioxo-1H-[1]-benzopyrano[3,4-b]pyridine-3-carboxylate (1.90 g; 56%) was obtained.

Analysis: calculated for $C_{11}H_{15}NO_5$: C 63.16; H 3.89; N 4.91. found C 62.98; H 3.92; N 5.07. $^1$H-NMR (TFA)δ/ppm: 1.2(t, CH$_3$); 4.3 (q, CH$_2$); 7.3–8.0 (m, Ar H); 8.4 (s, Py H); 11.3(s, NH).

EXAMPLE 3

Diethyl-1,5,8-trihydro-1,5,8-trioxo-4, 11H-[1]-benzopyrano[3,4-b]-[7,6-c]dipyridine-2,9-dicarboxylate

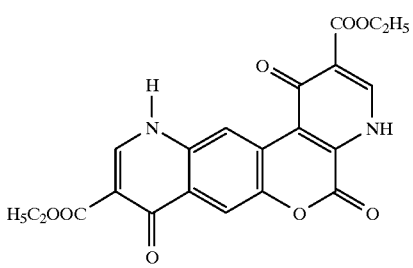

It was prepared according to the method disclosed in Example 1 starting from tetraethyl-{[(2-oxo-2H-[1]-benzopyrano-3,6-diyl)diamino]dimethylene} malonate (2.00 g; 3.872 mole). Duration of the reaction: 50 minutes. The obtained diethyl-1,5,8-trihydro-1,5,8-trioxo-4,11H-[1]-benzopyrano[3,4-b][7,6-c]dipyridine-2,9-dicarboxylate of brown colour was recrystallized from absolute ethanol (1.43 g; 87%). M.p.: 175–177° C.

Analysis: calculated for $C_{21}H_{16}N_2O_5$ C 59.43; H 3.80; N 6.60. found C 59.72; H 3.89; N 6.89. $^1$H-NMR (DMSO-$d_6$) δ/ppm: 1.3 (2t, 2 $CH_3$); 4.2 (2 q, 2 $CH_2$); 7–10 (m, CH, Ar H, Py H); 10.6 and 12.3 (2 d, 2 NH).

EXAMPLE 4
Ethyl-4,7-dihydro-4,7-dioxo-1H-[1]-benzopyrano[6,7-b]pyridine-3-carboxylate

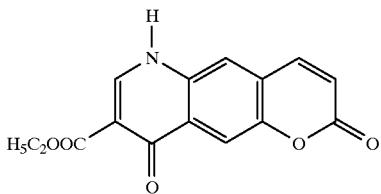

It was prepared according to the method disclosed in Example 1 starting from diethyl-{[(2-oxo-2H-[1]-benzopyrano-3-yl)amino]methylene} malonate (3.10 g; 9.357 mmole). Duration of the reaction: 45 minutes. The obtained yellow brown precipitate of ethyl-4,7-dihydro-4,7-dioxo- 1H-[1]-benzopyrano[6,7-b]pyridine-3-carboxylate was recrystallized from N,N-dimethylformamide (2.23 g; 84%). M.p. >300° C.

Analysis: calculated for $C_{15}H_{11}NO_5$ C 63.16; H 3.89; N 4.91. found C 63.05; H 3.92; N 4.88. $^1$H-NMR (DMSO-$d_6$) δ/ppm: 1.3 (t, $CH_3$); 4.2 (q, $CH_2$); 6.5 (d, H8), 7.4–8.0. (m, Ar H, Py H); 8.4 (d, H9); 10.7 (d, NH). m/z: 284 (M$^-$), 258, 256, 239, 212, 183, 127, 79.

EXAMPLE 5
Ethyl-4,7-dihydro-4,7-dioxo-3-hydroxy- H-[1]-benzopyrano[6,7-b]pyridine-3-carboxylate

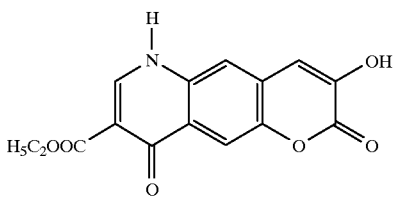

It was prepared according to the method disclosed in Example 1 starting from diethyl-{[(3-hydroxy-2-oxo-2H-[1]-benzopyrano-6-yl)amino]methylene} malonate (3.63 g; 0.011 mole). Duration of the reaction: 15 minutes. A light yellow brown precipitate of ethyl-4,7-dihydro-4,7-dioxo-3-hydroxy- 1H-[1]-benzopyrano[6,7-b] pyridine-3-carboxylate (3.63 g; 95%) was obtained. M.p. >300° C.

Analysis: calculated for $C_{15}H_{11}NO_6$ C 59.80; H 3.68; N 4.65. found C 59.66; H 3.61; N 4.27. $^1$H-NMR (DMSO-$d_6$) δ/ppm: 1.3 (t, $CH_3$); 4.2 (q, $CH_2$); 7.2–9.3 (m, Ar H, Py H); 10.7 (s, OH); 12.4 (s, NH). m/z: 300 (M$^-$), 273, 272, 255, 227, 178, 136, 91, 68, 54.

EXAMPLE 6
Ethyl-1,7-dihydro-1,7-dioxo-9-methyl-4H-[1]-benzopyrano [6,7-b]pyridine-2-carboxylate

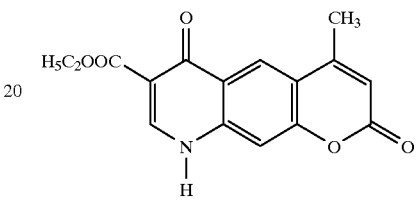

It was prepared according to the method disclosed in Example 1 starting from diethyl-{[(4-methyl-2-oxo-2H-[1]-benzopyrano-7-yl)amino]methylene} malonate (5.70 g; 0.017 mole). Duration of the reaction: 10 minutes. A gray brown precipitate of ethyl-1,7-dihydro-1, 7-dioxo-9-methyl-4H-[1 ]-benzopyrano[6,7-b]pyridine-2-carboxylate (3.43 g; 69%) was obtained. M.p. >300° C.

Analysis: calculated for $C_{16}H_{13}NO_5$ C 64.21; H 4.38; N 4.68. found C 64.36; H 4.14; N 4.50. $^1$H-NMR (DMSO-$d_6$) δ/ppm: 1.3 (s, $CH_3$); 2.1 (t, $CH_3$); 4.1 (q, $CH_2$); 6.2 (d, H8); 7.4 (d, H5); 7.7 (t, H10); 10.3 (s, Py H); 12.4 (bs, NH).

EXAMPLE 7
Ethyl-4,7-dihydro-4,7-dioxo-9-(trifluromethyl)-1H-[1]-benzopyrano[6,7-b]-pyridine-2-carboxylate

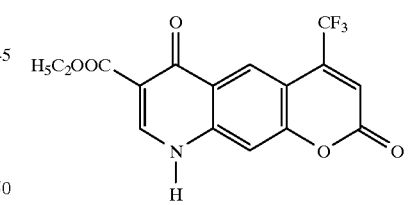

It was prepared according to the method disclosed in Example 1 starting from diethyl-{[(4-(trifluoromethyl)-2-oxo-2H-1]-benzopyrano-7-yl)amino]methylene} malonate (2.00 g; 0.005 mole). Duration of the reaction: 15 minutes. A light yellow precipitate of the ester (1.67 g; 94%) was obtained. M.p. >300° C.

Analysis: calculated for $C_{16}H_{10}F_3NO_5$ C 54.40; H 2.85; N 3.97. found C 54.41; H 2.97; N 3.86. $^1$H-NMR (DMSO-$d_6$) δ/ppm: 1.3 (t, $CH_3$); 4.2 (q, $CH_2$); 7.0 (d, H8); 7.4 (s, H5); 7.9 (d, H10); 8.5 (d, Py H); 12.4 (bs, NH).

EXAMPLE 8
Ethyl-1,6-dihydro-1,6-dioxo-7-hydroxy-4H-[1]-benzopyrano[7,8-b]pyridine-2-carboxylate

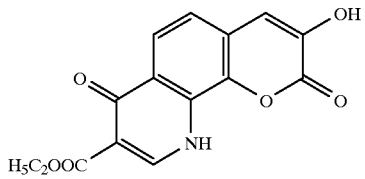

It was prepared according to the method disclosed in Example 1 starting from diethyl-{[(3-hydroxy-2-oxo-2H-[1]-benzopyrano-8-yl)amino]methylene} malonate (3.15 g; 9.070 mole). Duration of the reaction: 40 minutes. Ethyl-1,6-dihydro-1,6-dioxo-7-hydroxy-4H-[1]-benzopyrano[7,8-b]pyridine-2-carboxylate of orange brown colour (2.35 g; 86%) was obtained. M.p. >300° C.

Analysis: calculated for $C_{15}H_{11}NO_6$ C 59.80; H 3.68; N 4.65. found C 59.45; H 3.29; N 4.28. $^1$H-NMR (DMSO-$d_6$) δ/ppm: 1.3 (t, $CH_3$); 4.2 (q, $CH_2$); 7.1–8.3 (m, Ar H, Py H); 10.4 (s, OH); 11.8 (s, NH). m/z: 302 ($M^+$), 171, 155, 141.

EXAMPLE 9

Ethyl-1,5-dihydro1,5-dioxo-9-nitro-4H-[1]-benzopyrano[3,4-b]pyridine-2-carboxylate

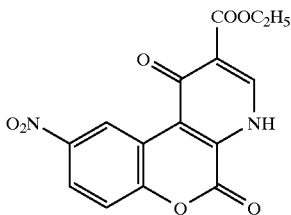

To a solution of ethyl-1,5-dihydro-1,5-dioxo-4H-[1]-benzopyrano[3,4-b]pyridine-2-carboxylate (0.81 g; 2.840 mmole) in concentrated sulfuric acid (3.73 g; 0.038 mole) which was cooled to 0–5° C., a mixture of nitric acid (d=1.4; 1.01 g; 0.016 mole) and concentrated sulfuric acid (1.96 g; 0.020 mole) was added drop by drop under stirring. The reaction mixture was stirred for another 10 minutes after attaining room temperature and then it was poured to a water-ice mixture. The obtained ethyl-1,5-dihydro-1,5-dioxo-9-nitro-4H-[1]-benzopyrano[3,4-b]pyridine-2-carboxylate was recrystallized from ethanol (0.89 g; 95%). M.p.: 246–247° C.

Analysis: calculated for $C_{15}$; $H_{10}N_2O_7$ C 54.55; H 3.05; N 8.48. found C 54.50; H 2.87; N 8.65. $^1$H-NMR (TFA)δ/ppm: 1.2 (t, $CH_3$); 4.3 (q, $CH_2$); 7.4 (d, H7); 8.3 (d, H8); 9.1 (s, H10); 9.6 (s, Py H); 11.3 (s, NH). m/z: 329 ($M^-$), 313, 301, 284, 269, 257, 256, 241, 228, 151.

EXAMPLE 10

Ethyl1,5-dihydro1,5-dioxo-9-amino-4H-[1]-benzopyrano[3,4-b]pyridine-2-carboxylate

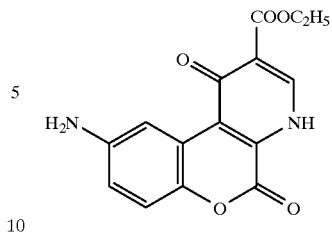

To a solution of ethyl-1,5-dihydro-1,5-dioxo-9-nitro-4H-[1]-benzopyrano[3,4-b]-pyridine-2-carboxylate (0.50 g; 1.514 mmole) in glacial acetic acid (150 ml) a catalyst (4.92% Pd/C; 0.15 g) was added and the reduction took place for 6 hours under hydrogen stream of 3 bar. After the completion of the reaction acetic acid was evaporated from the filtered reaction mixture. The obtained amine (0.59 g; 100%) was recrystallized from glacial acetic acid. M.p.: 270–272° C.

Analysis: calculated for $C_{15}H_{22}N_2OxC_2H_4O_2$ C 58.18; H 4.28; N 8.48. found C 57.94; H 4.14; N 8.24. $^1$H-NMR (TFA)δ/ppm: 1.3 (t, $CH_3$); 4.4 (q, $CH_2$); 7.4–7.8 (m, Ar H); 9.2 (m, Py H); 11.3 (s, NH).

EXAMPLE 11

1,5-dihydro1,5-dioxo-7-fluoro-4H-[1]-benzopyrano[3,4-b]pyridine-2-carboxylic acid

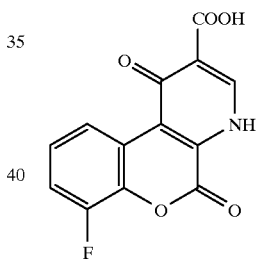

A solution of ethyl-1,5-dihydro-1,5-dioxo-7-fluoro-4H-[1]-benzopyrano[3,4-b]-pyridine-2-carboxylate (1.70 g; 5.606 mmole) in a 10% aqueous sodium hydroxide solution (22 ml) was heated for 90 minutes at the boiling temperature and then it was boiled for about 5 minutes with active carbon. In the filtrate the acid was precipitated with a 10% aqueous hydrochloric acid solution (up to pH 2–3) and the cooled solution was left to stand for a few hours at +4° C. The obtained light yellow precipitate of the acid (1.50 g; 97%) was recrystallized from an ethyl acetate/ethanol mixture (1:1) or from N,N-dimethylformamide. M.p. >300° C.

Analysis: calculated for $C_{13}H_6FNO_5$ C 56.74; H 2.20; N 5.09. found C 56.52; H 1.84; N 5.11. 1H-NMR (TFA)δ/ppm: 7.3–7.4 (m, 3 Ar H); 8.7 (m, Py H); 9.2 (s, NH); 11.3 (s, COOH).

EXAMPLE 12

4,5-dihydro-4,5-dioxo-4H-[1]-benzopyrano[4,3-b]pyridine-3-carboxylic acid

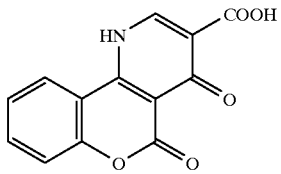

A solution of ethyl-4,5-dihydro-4,5-dioxo-4H-[1]-benzopyrano[4,3-b]pyridine-3-carboxylate (1.90 g; 6.661 mmole) in 1M sodium hydroxide (50 ml) was heated for 90 minutes at boiling temperature and then shortly boiled with active carbon, it was filtered and the filtrate was acidified with a 10% aqueous hydrochloric acid solution (up to pH 2–3) and the acid was precipitated (1.54 g; 95%). M.p.>300° C.

Analysis: calculated for $C_{13}H_7NO_5$ C 60.70; H 2.74; N 5.45 found C 60.37; H 2.43; N 5.51. $^1$H-NMR (DMSO-$d_6$) δ/ppm: 7.5 (d, H7); 7.8 (t, H9); 8.4 (d, H10); 8.7 (m, H8,Py H); 9.2 (s, NH); 11.3 (s, COOH). m/z: 256 (M$^-$), 240, 239, 223, 212, 211, 183, 120, 82.

EXAMPLE 13
1,5,8-trihydro-1,5,8-trioxo-4,1 1H-[1]-benzopyrano[3,4-b][] 7,6-c]dipyridine-2,9-dicarboxylic diacid

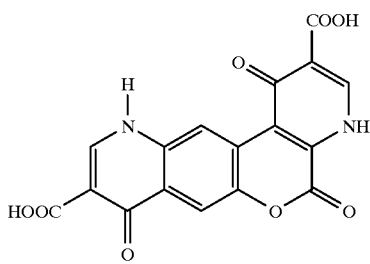

It was prepared according to the method disclosed in Example 12 starting from diethyl-1,5,8-trihydro-1,5,8-trioxo-4,11H-[1]-benzopyrano[3,4-b][7,6-c]dipyridine-2,9-dicarboxylate (0.90 g; 121 mmole). Duration of the reaction: 45 minutes. The obtained acid was of yellow brown colour (0.45 g; 58%). M.p. >300° C.

Analysis: calculated for $C_{17}H_8N_2O_8$ C 55.44; H 2.19; N 7.61. found C 55.22; H 2.58; N 7.50. 1H-NMR (DMSO-$d_6$) δ/ppm: 7.1–9.5 (m, Ar H, Py H); 12.3 (d, 2 NH); 14.8 (s, COOH); 15.4 (s, COOH). m/z: 368 (M$^+$), 341, 264, 256, 213, 198, 188, 156, 137, 129, 91, 81, 69.

EXAMPLE 14
4,7-dihydro-4,7-dioxo-1H-[1]-benzopyrano[6,7-b]pyridine-3-carboxylic acid

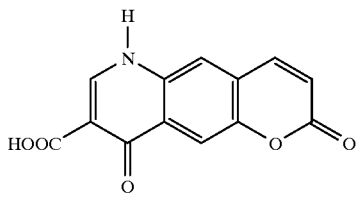

It was prepared according to the method disclosed in Example 11 starting from ethyl-4,7-dihydro-4,7-dioxo-1H-[1]-benzopyrano[6,7-b]pyridine-3-carboxylate (1.10 g; 3.856 mmole). Duration of the reaction: 3 hours. A light yellow precipitate of the acid (0.84 g; 85%) was obtained. M.p. >300° C.

Analysis: calculated for $C_{13}H_7NO_5$ C 60.70; H 2.74; N 5.45. found C 60.37; H 2.80; N 5.76. m/z: 258 (M$^+$), 254, 249, 213, 151, 138, 125, 109, 98, 74, 62.

EXAMPLE 15
4,7-dihydro-4,7-dioxo-8-hydroxy-1H-[1]-benzopyrano[6,7-b]pyridine-3-carboxylic acid

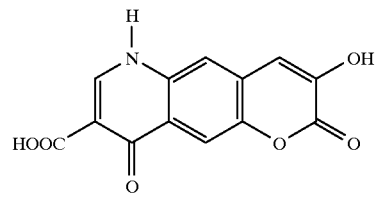

It was prepared according to the method disclosed in Example 12 starting from ethyl-4,7-dihydro-4,7-dioxo-8-hydroxy-1H-[1]-benzopyrano[6,7-b]pyridine-3-carboxylate (2.83 g; 9.394 mmole). Duration of the reaction: 3 hours. A yellow precipitate of the acid (2.13 g; 83%) was obtained. M.p. >300° C. 1H-NMR (DMSO-$d_6$)δ/ppm: 7.6–8.7 (m, Ar H); 9.4 (s, Py H); 13.4 (s, NH); 15.2 (s, COOH). m/z: 273 (M$^+$), 256, 239, 229,181, 125, 114, 95, 73.

EXAMPLE 16
1,7-dihydro-1,7-dioxo-9-methyl-4H-[1]-benzopyrano[6,7-b]pyridine-2-carboxylic acid

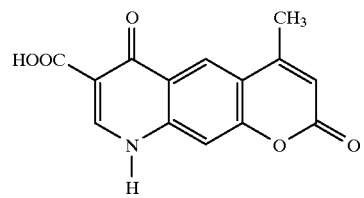

It was prepared according to the method disclosed in Example 11 starting from ethyl-1,7-dihydro-1,7-dioxo-9-methyl-4H-[1]-benzopyrano[6,7-b]pyridine-2-carboxylate (3.40 g; 0.011 nmole). Duration of the reaction: 20 minutes. The obtained precipitate of gray white colour was recrystallized from N,N-dimethylformamide (2.32 g; 75%).

Analysis: calculated for $C_{14}H_9NO_5 \cdot xC_3H_7NO$ C 59.30; H 4.68; N 8.14. found C 59.50; H 4.61; N 7.81. $^1$H-NMR (DMSO-$d_6$)δ/ppm: 1.9 (s, CH$_3$); 6.3 (s, H8); 7.6 (d, H5); 8.0 (s, H10);

9.0 (s, Py H); 13.2 (bs, NH); 14.9 (s, COOH).

EXAMPLE 17
1,7-dihydro-1,7-dioxo-9-(trifluromethyl)-4H-[1]-benzopyrano[6,7-b]pyridine-2-carboxylic acid

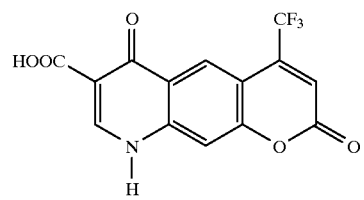

It was prepared according to the method disclosed in Example 12 starting from ethyl-1,7-dihydro-1,7-dioxo-9-(trifluromethyl)-4H-[1]-benzopyrano[(6,7-b]pyridine-2-carboxylate (1.40 g; 3.963 mmole). Duration of the reaction:

2 hours. The obtained acid was recrystallized from the N,N-dimethylformamide/ethanol mixture (1.28 g; 99%). M.p. >300° C.

Analysis: calculated for $C_{14}H_6F_3NO_5$ C 51.70; H 1.86; N 4.31. found C 51.48; H 1.82; N 4.27. $^1$H-NMR (DMSO-$d_6$) δ/ppm: 7.2 (s, H8); 7.8 (s, H5); 8.6 (s, H10); 9.0 (s, Py H); 13.4 (bs, NH); 14.5 (bs, COOH).

EXAMPLE 18
1,5-dihydro-1,5-dioxo-7-hydroxy-4H-[1]-benzopyrano[7,8-b]pyridine-2-carboxylic acid

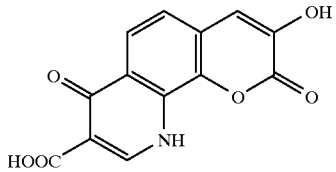

It was prepared according to the method disclosed in Example 13 starting from ethyl-1,5-dihydro1,5-dioxo-7-hydroxy-4H-[1]-benzopyrano [7,8-b]pyridine-2-carboxylate (2.12 g; 7.037 mmole). Duration of the reaction: 3 hours. A green brown acid (1.27 g; 66%) was obtained. M.p. >300° C. $^1$H-NMR (DMSO-$d_6$)δ/ppm: 7.1–7.8 (m, Ar H, Py H); 8.6 (s, OH); 10.6 (s, NH); 15.2 (s, COOH). m/z: 273 (M$^+$), 212, 179, 81, 79, 61, 59, 45, 43.

We claim:

1. A coumarin quinolone carboxylic acid wherein the pyridone system is fused in 3,4-, 6,7- and 7,8-positions of the coumarin system, of the formula I

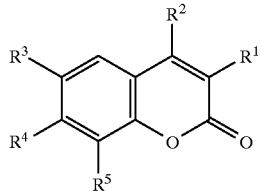

wherein $R^1R^2$=—NHCH=C(CO$_2$R$^6$)CO, $R^3$=NO$_2$ or NH$_2$,$R^4$=R$^5$= H, $R^6$=H or C$_2$H$_5$;

$R^1R^2$=—NHCH=C(CO$_2$R$^6$)CO, $R^3$=R$^4$=H,R$^5$=F, R$^6$=H or C$_2$H$_5$;

$R^1R^2$=—CO(CO$_2$R$^6$)C=CHNH, $R^3$=R$^4$=R$^5$=H, R$^6$=H or C$_2$H$_5$;

$R^1R^2$=R$^3$R$^4$=—NHCH=C(CO$_2$R$^6$) CO, R$^5$=H, R$^6$=H or C$_2$H$_5$;

$R^1$=H or OH, R$^2$=R$^5$=H, R$^3$R$^4$=—NHCH=C(CO$_2$R$^6$) CO, R$^6$=H or C$_2$H$_5$;

$R^1$=OH, $R^2$=R$^3$=H, R$^4$R$^5$=—CO(CO$_2$R$^6$) C=CHNH, R$^6$=H or C$_2$H$_5$;

$R^1$=R$^5$=H, $R^2$=CH$_3$or CF$_3$, R$^3$R$^4$=—CO(CO$_2$R$^6$)C=CHNH, R$^6$=H or C$_2$H$_5$, or a pharmaceutically acceptable salt thereof.

2. The compound of the formula I according to claim 1, wherein $R^1R^2$=—NHCH=C(CO$_2$C$_2$H$_5$)CO, $R^3$=R$^4$=H, R$^5$=F.

3. The compound of the formula I according to claim 1, wherein $R^1R^2$=—CO(CO$_2$C$_2$H$_5$)C=CHNH, $R^3$=R$^4$=R$^5$=H.

4. The compound of the formula I according to claim 1, wherein $R^1R^2$=R$^3$R$^4$=—NHCH=C(CO$_2$C$_2$H$_5$)CO, R$^5$=H.

5. The compound of the formula I according to claim 1, wherein $R^1$=H, $R^2$=R$^5$=H, R$^3$R$^4$=—NHCH=C(CO$_2$C$_2$H$_5$) CO.

6. The compound of the formula I according to claim 1, wherein $R^1$=OH, $R^2$=R$^5$=H, R$^3$R$^4$=—NHCH=C(CO$_2$C$_2$H$_5$) CO.

7. The compound of the formula I according to claim 1, wherein $R^1$=R$^5$=H, $R^2$=CH$_3$, R$^3$R$^4$=—CO(CO$_2$C$_2$H$_5$)C=CHNH.

8. The compound of the formula I according to claim 1, wherein $R^1$=R$^3$=R$^5$=H, $R^2$=CF$_3$, R$^4$=—NHCH=C(CO$_2$C$_2$H$_5$)$_2$.

9. The compound of the formula I according to claim 1, wherein $R^1$=OH, $R^2$=R$^3$=H, R$^4$R$^5$=—CO(CO$_2$C$_2$H$_5$)C=CHNH.

10. The compound of the formula I according to claim 1, wherein $R^1R^2$=—NHCH=C(CO$_2$C$_2$H$_5$)CO, $R^3$=NO$_2$, R$^4$=R$^5$=H.

11. The compound of the formula I according to claim 1, wherein $R^1R^2$=—NHCH=C(CO$_2$C$_2$H$_5$)CO, $R^3$=NH$_2$, R$^4$=R$^5$=H.

12. The compound of the formula I according to claim 1, wherein $R^1R^2$=—NHCH=C(CO$_2$H)CO, $R^3$=R$^4$=H, R$^5$=F.

13. The compound of the formula I according to claim 1, wherein $R^1R^2$=—CO(CO$_2$H)C=CHNH, $R^3$=R$^4$=R$^5$=H.

14. The compound of the formula I according to claim 1, wherein $R^1R^2$=R$^3$R$^4$=—NHCH=C(CO$_2$H)CO, R$^5$=H.

15. The compound of the formula I according to claim 1, wherein $R^1$=H, $R^2$=R$^5$=H, R$^3$R$^4$=—NHCH=C(CO$_2$H)CO.

16. The compound of the formula I according to claim 1, wherein $R^1$=OH, $R^2$=R$^5$=H, R$^3$R$^4$=—NHCH=C(CO$_2$H)CO.

17. The compound of the formula I according to claim 1, wherein $R^1$=R$^5$=H, $R^2$=CH$_3$, R$^3$R$^4$=—CO(CO$_2$H)C=CHNH.

18. The compound of the formula I according to claim 1, wherein $R^1$=R$^3$=R$^5$=H, $R^2$=CF$_3$, R$^4$=—NHCH=C(CO$_2$H)$_2$.

19. The compound of the formula I according to claim 1, wherein $R^1$=OH, $R^2$=R$^3$=H, R$^4$R$^5$=—CO(CO$_2$H)CHNH.

20. The compound of claim 1 wherein $R^1R^2$=—NHCH(CO$_2$R$^6$))CO,R$^3$=NO$_2$ or NH$_2$, R$^4$=R$^5$= H, R$^6$=H or C$_2$H$_5$; or $R^1R^2$=—NHCH(CO$_2$R$^6$)CO, $R^3$=R$^4$=H, R$^5$ =F, R$^6$=H or C$_2$H$_5$; or $R^1R^2$=—CO(CO$_2$R$^6$)CHNH, $R^3$=R$^4$=R$^5$=H, R$^6$=H or C$_2$H$_5$.

* * * * *

UNITED STATES PATENT AND TRADEMARK OFFICE
CERTIFICATE OF CORRECTION

PATENT NO. : 5,908,933
DATED : June 1, 1999
INVENTOR(S) : Mladen Trkovnik et al.

Page 1 of 1

It is certified that error appears in the above-identified patent and that said Letters Patent is hereby corrected as shown below:

Claim 8 reads "The compound of the formula I according to claim 1, wherein $R^1 = R^3 = R^5 = H$, $R^2 = CF_3$, $R^4 = -NHCH=C(CO_2C_2H_5)_2$." and should be amended to read -- The compound of the formula I according to claim 1, wherein $R^1 = R^5 = H$, $R^2 = CF_3$, $R^3R^4 = -CO(CO_2C_2H_5)CHNH$. --

Claim 18 reads "The compound of the formula I according to claim 1, wherein $R^1 = R^3 = R^5 = H$, $R^2 = CF_3$, $R^4 = NHCH-C(CO_2H)_2$" and should be amended to read -- The compound of the formula I according to claim 1, wherein $R^1 = R^5 = H$, $R^2 = CF_3$, $R^3R^4 = -CO(CO_2H)CHNH$. --

Signed and Sealed this

Nineteenth Day of March, 2002

Attest:

JAMES E. ROGAN
*Director of the United States Patent and Trademark Office*

*Attesting Officer*

UNITED STATES PATENT AND TRADEMARK OFFICE
CERTIFICATE OF CORRECTION

PATENT NO.     : 5,908,933
DATED          : June 1, 1999
INVENTOR(S)    : Mladen Trkovnik et al.

It is certified that error appears in the above-identified patent and that said Letters Patent is hereby corrected as shown below:

Column 12,
Lines 18-20, reads "The compound of the formula I according to claim 1, wherein $R^1 = R^3 = R^5 = H$, $R^2 = CF_3$, $R^4 = -NHCH=C(CO_2C_2H_5)_2$." and should be amended to read -- The compound of the formula I according to claim 1, wherein $R^1 = R^5 = H$, $R^2 = CF_3$, $R^3R^4 = -CO(CO_2C_2H_5)CHNH$. --

Column 12,
Lines 44-45, reads "The compound of the formula I according to claim 1, wherein $R^1 = R^3 = R^5 = H$, $R^2 = CF_3$, $R^4 = NHCH-C(CO_2H)_2$" and should be amended to read -- The compound of the formula I according to claim 1, wherein $R^1 = R^5 = H$, $R^2 = CF_3$, $R^3R^4 = -CO(CO_2H)CHNH$. --

Signed and Sealed this

Twenty-first Day of October, 2003

JAMES E. ROGAN
*Director of the United States Patent and Trademark Office*